United States Patent
Steppel et al.

(10) Patent No.: US 9,090,776 B2
(45) Date of Patent: Jul. 28, 2015

(54) SQUARYLIUM DYES

(71) Applicant: Exciton, Inc., Dayton, OH (US)

(72) Inventors: Richard N. Steppel, Dayton, OH (US); Larry E. Knaak, Dayton, OH (US); Paul A. Cahill, Dayton, OH (US)

(73) Assignee: Exciton, Inc., Dayton, OH (US)

( * ) Notice: Subject to any disclaimer, the term of this patent is extended or adjusted under 35 U.S.C. 154(b) by 77 days.

(21) Appl. No.: 14/017,359

(22) Filed: Sep. 4, 2013

(65) Prior Publication Data
US 2014/0061505 A1    Mar. 6, 2014

Related U.S. Application Data

(60) Provisional application No. 61/696,481, filed on Sep. 4, 2012.

(51) Int. Cl.
*C09B 57/00* (2006.01)
*G01N 21/64* (2006.01)

(52) U.S. Cl.
CPC ........ *C09B 57/007* (2013.01); *G01N 21/6428* (2013.01)

(58) Field of Classification Search
CPC ................ G01N 21/6428; C07D 209/02
USPC ........................ 250/459.1; 548/455
See application file for complete search history.

(56) References Cited

U.S. PATENT DOCUMENTS

| 5,543,086 A | 8/1996 | Bertelson et al. |
| 2013/0147345 A1* | 6/2013 | Maeda et al. ............... 313/503 |

FOREIGN PATENT DOCUMENTS

JP    2012-008532 A    1/2012

* cited by examiner

*Primary Examiner* — David Porta
*Assistant Examiner* — Hugh H Maupin
(74) *Attorney, Agent, or Firm* — Wood, Herron & Evans, LLP

(57) ABSTRACT

Squarylium dyes with improved design flexibility via functionalization thereof thereby yielding desirable photophysical, solubility, thermal stability, and/or light stability properties, for example. The resulting dyes are useful in optical filters and as fluorescent indicators, for example.

21 Claims, 1 Drawing Sheet

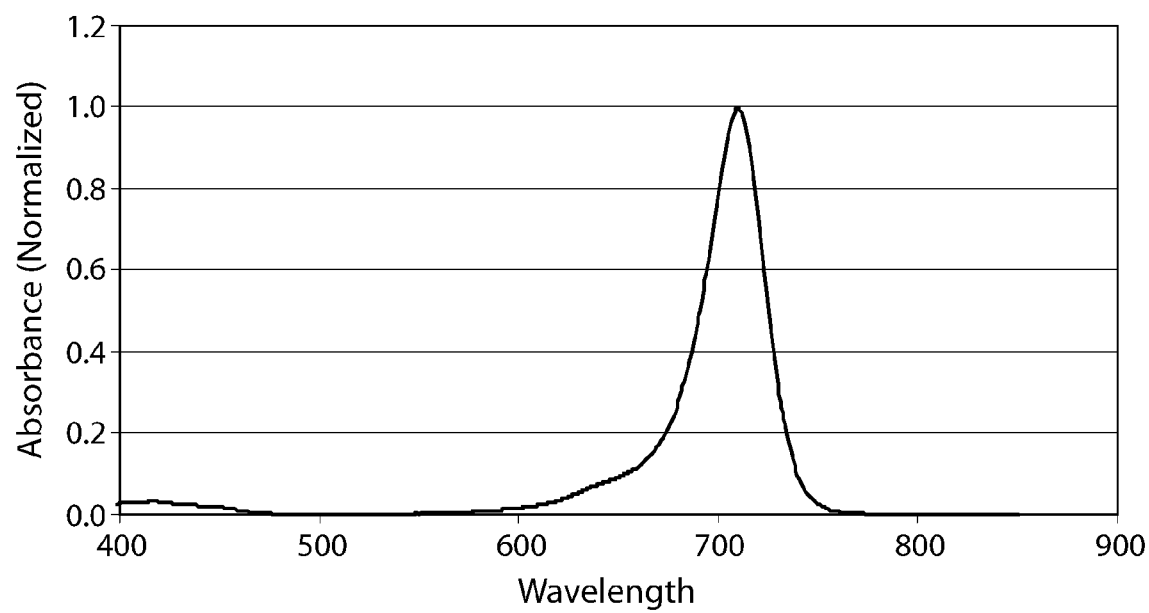

SQUARYLIUM DYES

CROSS REFERENCE TO RELATED APPLICATION

This application claims the benefit of U.S. Provisional Application No. 61/696,481, filed Sep. 4, 2012, the disclosure of which is hereby incorporated by reference herein in its entirety.

TECHNICAL FIELD

The present invention relates to squarylium dyes, methods of synthesis, and uses thereof.

BACKGROUND

Squarylium dyes, or squaraines, which were first reported in the 1960's (A Treibs and K. Jacob, Liebigs Ann. Chem. 1966, 592, 153; H. E. Sprenger and W. Ziegenbein, Angew. Chem. Int. Ed. Engl. 1966, 5, 894), are a class of often-fluorescent dyes with peak absorption wavelength ranging from mid-visible into infrared wavelengths (for a review, see J. Fabian, Chem. Rev. 1992, 92, 1197 and cited references). Squarylium dyes have been investigated for many applications. Such applications include uses as photoconducting layers for xerography (K. Y. Law, Chem. Rev. 1993, 93, 449), light filters (R. Bertelson and R. Sallavanti, U.S. Pat. No. 5,543,086), infrared wavelength emitting fluorescent dyes (K. Y. Law, J. Phys. Chem. 1987, 91, 5184), biological probes (E. Terpetschnig, H. Szmacinski and J. R. Lakowicz, J. Fluorescence 1993, 3, 153), and nonlinear optics (C. W. Dirk et al., J. Am. Chem. Soc. 1995, 117, 2214). Squarylium dyes are generally prepared from squaric acid and a nitrogen base, often in an alcohol solvent, by azeotropic distillation of water, and collected by filtration as described in the references above.

Long-wavelength red and near infrared wavelength absorbing dyes are represented by many different types of structures, among them dithiolenes, cyanines, squaryliums, croconiums, anthraquinones, phthalocyanines, naphthalocyanines, rylenes, mono-cationic aminium salts, di-cationic diimmonium salts, inter alia (J. Fabian, Chem. Rev. 1992, 92, 1197). Some of these red and infrared wavelength absorbing dyes also show red and infrared wavelength emission.

The squarylium dye structure offers many sites for functionalization. For example in formula (I) below, X may be chosen, for example, from H, —OH, halogen, or alkyl, and the R groups on the nitrogen may simultaneously be the same or different and chosen, for example, from H, alkyl, aryl, or alkylaryl. Furthermore, the R groups may form a cyclic structure with the arene, as described in U.S. Pat. No. 5,543,086, the contents of which is expressly incorporated by reference herein in its entirety, one example of which is compound (II) below. One or more of the positions ortho- to the nitrogen atoms in formula (I) may also be substituted with heteroatoms or other groups.

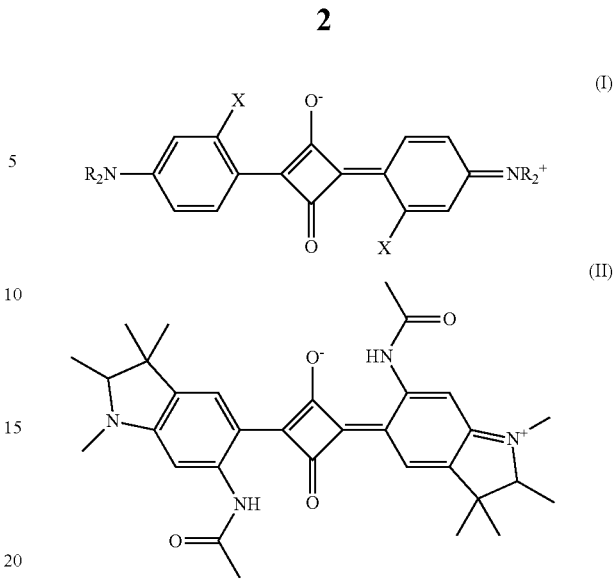

It would be beneficial to provide squarylium dyes with improved design flexibility via functionalization thereof thereby yielding desirable photophysical, solubility, thermal stability, and/or light stability properties, for example. Highly soluble squarylium dyes are desirable, as the low solubility of many squarylium dyes may be a limiting factor in many applications. For example, the solubilities of squarylium dyes derived from m-dialkylaminophenols are <10 gm/L in many common solvents, and <1 gm/L in some alcohols.

SUMMARY

The present invention is directed to squarylium dyes, methods of synthesis, and uses thereof.

In accordance with an embodiment of the invention, a squarylium dye is provided having the formula (III)

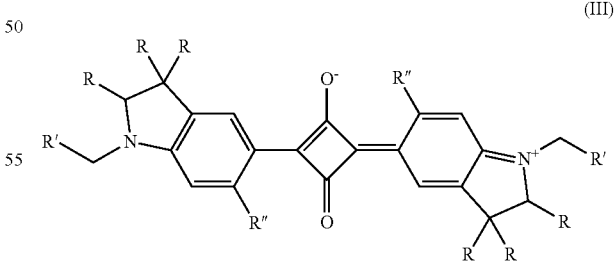

wherein each R group is independently selected from the group consisting of hydrogen, alkyl, and alkylether, wherein at least three R groups are not hydrogen;

each R' group is independently selected from the group consisting of alkyl, aryl, alkylsulfonate, arylsulfonate, alkylcarboxylate, and arylcarboxylate;

each R" group is independently selected from the group consisting of amine, sulfonamide, carbamate, amide, urea, and hydroxyl, wherein when each R' group is alkyl, both R" groups cannot be an amide;

and mixtures thereof.

In accordance with another embodiment of the invention, a squarylium dye mixture is formed by reacting three or more amine bases with squaric acid or a derivative thereof to yield a mixture of squarylium dyes, wherein the solubility of the squarylium dye mixture is 5 or more times greater than the solubility of the least soluble symmetric squarylium dye in the mixture.

In accordance with another embodiment of the invention, a method for increasing the solubility of a squarylium dye is provided in which three or more amine bases are reacted with squaric acid or a derivative thereof to yield a mixture of squarylium dyes. The solubility of the squarylium dye mixture is 5 or more times greater than the solubility of the least soluble symmetric squarylium dye in the mixture.

In accordance with yet another embodiment of the invention, a method for authentication or identification of an article is provided that includes illuminating an article including a squarylium dye having the formula (III) and detecting emission thereof.

In yet another embodiment, a method for authentication or identification of an article is provided that includes illuminating an article including a squarylium dye mixture formed by reacting three or more amine bases with squaric acid or a derivative thereof to yield a mixture of squarylium dyes, wherein the solubility of the squarylium dye mixture is 5 or more times greater than the solubility of the least soluble symmetric squarylium dye in the mixture, and detecting emission thereof.

BRIEF DESCRIPTION OF THE DRAWING

The accompanying drawing, which is incorporated in and constitutes a part of this specification, illustrates an embodiment of the invention and, with a detailed description of the embodiments given below, serves to explain the principles of the invention.

The FIGURE is an absorption spectrum of the ortho-, ortho- isomer of compound (IV) in dichloromethane ($CH_2Cl_2$), with the peak absorption wavelength being about 710 nm for all isomers.

DETAILED DESCRIPTION OF SPECIFIC EMBODIMENTS

The present invention is directed to squarylium dyes of the general formula (III), one resonance structure of which being shown below, which may be prepared from corresponding dihydroindole amine bases, as is further discussed below.

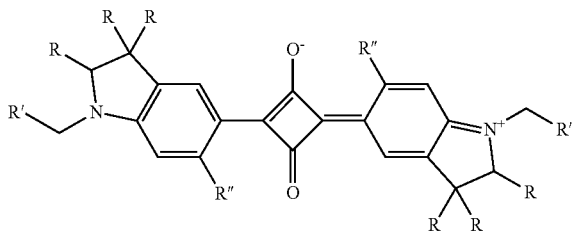

(III)

With respect to formula (III), each R group may be independently selected from hydrogen, an alkyl, or an alkylether. In one example, one or more hydrogen atoms of the alkyl may be substituted by an aryl, a sulfonate (e.g., an alkylsulfonate or arylsulfonate), or a carboxylate (e.g., an alkylcarboxylate or arylcarboxylate). In another example, at least three of the R groups cannot be hydrogen. In yet another example, at least one R group is alkyl, e.g., methyl. In still another example, when not hydrogen, R is methyl.

Each R' group may be independently selected from hydrogen, an aryl, alkylsulfonate, arylsulfonate, alkylcarboxylate, or arylcarboxylate. In one example, at least one R' group is aryl, e.g., a substituted or unsubstituted phenyl.

Each R" group may be independently selected from functional groups that are hydrogen bond donors including, but not limited to, amines (e.g., alkylamines or arylamines), sulfonamides, carbamates, ureas, amides (e.g., alkylamide or arylamides), or hydroxy. In another example, at least one R" group is a nitrogen-containing functional group such as amine, carbamate, amide, or sulfonylamide.

In one embodiment, each R group can be independently selected from the group consisting of hydrogen, alkyl, and alkylether, wherein at least three R groups are not hydrogen; each R' group can be independently selected from the group consisting of alkyl, aryl, alkylsulfonate, arylsulfonate, alkylcarboxylate, and arylcarboxylate; and each R" group can be independently selected from the group consisting of amine, sulfonamide, carbamate, amide, urea, and hydroxyl, wherein when each R' is alkyl, both R" groups cannot be an amide.

In another embodiment, at least one R" group can be selected from an amine defined by —$NR_aR_b$, where $R_a$ and $R_b$ are independently selected from hydrogen, substituted or unsubstituted alkyl, or substituted or unsubstituted aryl; an amide defined by —$NHCOR_e$, where $R_e$ is selected from a substituted or unsubstituted alkyl, a substituted or unsubstituted aryl, or a haloalkyl; a carbamate defined by —$NHCO_2R_f$, where $R_f$ is selected from a substituted or unsubstituted alkyl, a substituted or unsubstituted aryl, or a haloalkyl; a urea defined by —$NHCONR_gR_h$, where $R_g$ and $R_h$ are independently selected from hydrogen, a substituted or unsubstituted alkyl, a substituted or unsubstituted aryl, or a haloalkyl; or a sulfonamide defined by —$NHSO_2R_i$, where $R_i$ is selected from a substituted or unsubstituted alkyl, a substituted or unsubstituted aryl, or a haloalkyl.

In another embodiment, each R group is methyl, each R' group is substituted phenyl, and each R" group is an amide, a carbamate, or a sulfonylamide. In another example, each R" group is an arylamide.

In yet another embodiment, the squarylium dye has the chemical structure (IV) below wherein each R group is methyl, each R' group is benzamido phenyl (shown as a mixture of isomers), and each R" group is benzamide.

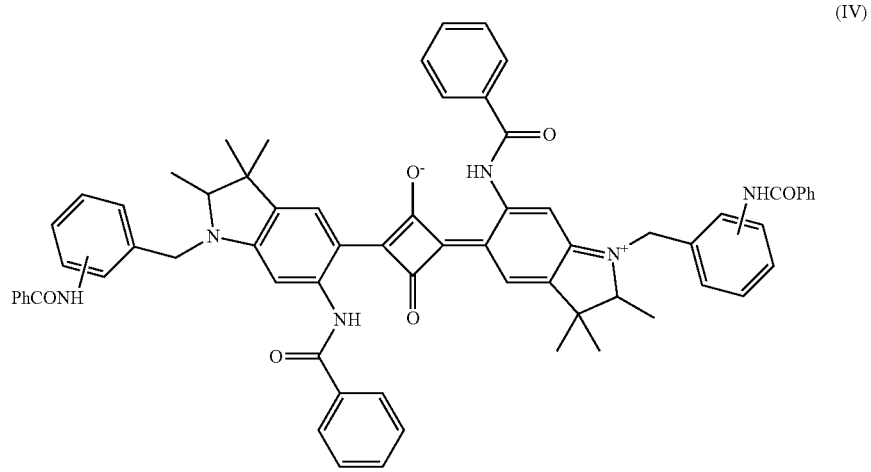

(IV)

In yet another embodiment, a mixture of dyes, all of similar peak absorption wavelength but different composition, are prepared from a mixture of amine bases, such as dihydroindole amine bases, in such a manner as to increase the solubility of the mixture of dyes significantly over that of a single isomer. In one example, the peak absorption wavelength for each dye can be from about 600 nm to about 850 nm or from about 630 nm to about 810 nm, with the wavelength of each dye in the mixture within ±50 nm of a desired wavelength. In another example, the wavelength of each dye in the mixture can be within ±30 nm of a desired wavelength. In the example of dye (IV), above, a mixture of 6 regioisomeric symmetric and asymmetric squarylium dyes may be prepared from 2-, 3-, and 4-benzamidophenyl substituted amine bases, and this mixture shows an unexpectedly higher solubility than any individual symmetric dye therein.

Furthermore, amine bases, shown by example, but not limited to the structures below for (IVa) through (IVd), many of which show similar peak absorption wavelengths when combined with squaric acid individually to form symmetric dyes, may be mixed and combined to give a mixture of dyes with higher solubility. In one example, three or more amine bases may be reacted with squaric acid or a derivative thereof to yield a mixture of squarylium dyes. Here, the solubility of the squarylium dye mixture can be 5 or more times greater than the solubility of the least soluble symmetric squarylium dye in the mixture. In another example, the solubility of the squarylium dye mixture can be 10 or more times greater than the solubility of the least soluble symmetric squarylium dye in the mixture. In one example, each amine base is at least 1% of the mixture of bases.

In some cases, substitution by trifluoroacetamide on a dihydroindole amine base yields a dye with a peak absorption wavelength similar to that observed with a dihydroindole amine base substituted by benzamide; similarly, substitution by trifluoromethanesulfonamide for acetamide yields dyes of similar wavelength.

As used herein, "alkyl" can include any branched or unbranched hydrocarbons. In one example, alkyl includes $C_1$-$C_6$ branched or unbranched hydrocarbons. Examples of suitable alkyls for use in formula (III) include, for example, methyl, ethyl, 1-methylethyl, propyl, 2-methylpropyl, butyl, and the like.

As used herein, "aryl" can include any resonance stabilized monocyclic, bicyclic, or tricyclic group of between 5 and 14 atoms in the ring structure, which may be further substituted by alkyl groups, other aryl groups, and functional groups. Examples of suitable aryls for use in formula (III) include, for example, phenyl, naphthyl, and anthracenyl, as well as heteroatom substituted aromatics represented by thienyl, pyridinyl, pyrazinyl, and the like.

As used herein, "haloalkyl" includes an alkyl group that is substituted with 1 or more independently chosen halogens (e.g., "$C_1$-$C_6$ haloalkyl" groups have from 1 to 6 carbon atoms). Examples of haloalkyl groups include, but are not limited to, mono-, di-, or tri-fluoromethyl; mono-, di-, or tri-chloromethyl; mono-, di-, tri-, tetra-, or penta-fluoroethyl; mono-, di-, tri-, tetra-, or penta-chloroethyl; and 1,2,2,2-tetrafluoro-1-trifluoromethyl-ethyl. In one example, the haloalkyl group is a trifluoromethyl or difluoromethyl.

Squarylium dyes of the general formula (III), such as that of structural formula (IV), may be prepared from mixtures of dihydroindole amine bases with any combination of ortho-, meta-, and para- substitution on the dihydroindole N-benzyl group. Examples of such dihydroindole amine bases that are suitable for condensation as single isomers or as mixtures are compounds IVa though IVd shown below. Although in each of the compounds IVa through IVd, below, both functional groups on each compound are the same, different functional groups on each compound may be applied, e.g., urea and amide, or any other combination.

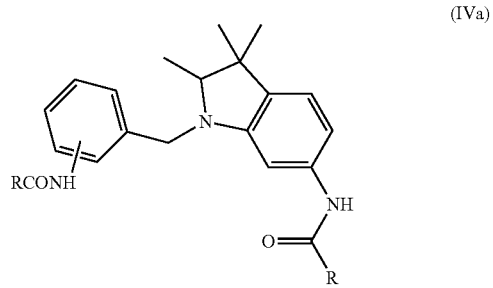

(IVa)

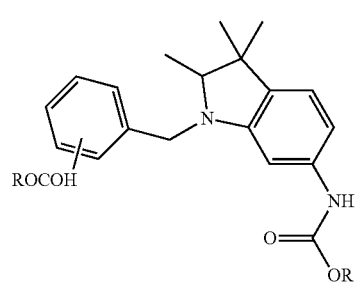
(IVb)

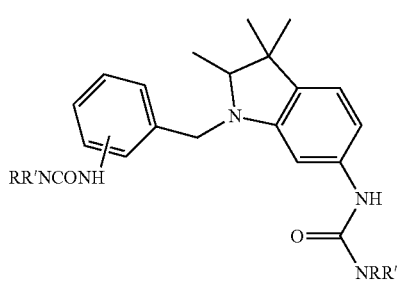
(IVc)

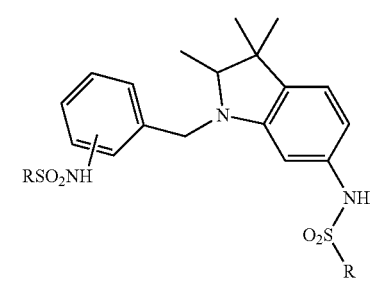
(IVd)

Each of these amine bases can be prepared as single isomers by alkylation of a dihydroindole with the appropriate nitro-benzyl bromide, reduction, and then reaction to form the corresponding amine, amide, carbamate, urea, or a sulfonamide, for example, which is discussed in detail below with respect to specific examples.

Non-limiting examples of methods of synthesis for the squarylium dyes of the general formula (III) in accordance with the description are now disclosed below. These examples are merely for the purpose of illustration and are not to be regarded as limiting the scope of the invention or the manner in which it can be practiced. Other examples will be appreciated by a person having ordinary skill in the art.

EXAMPLE 1

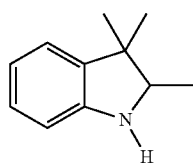

2,3,3-Trimethyl-dihydroindole, which is shown above, was prepared in two steps from 2,3,3-trimethyl-3H-indole. Reduction of 7.96 gm of 2,3,3-trimethyl-3H-indole was first carried out in a 500 mL Parr shaker with 50 mL ethanol solvent, 100 mg of 10% Pd/C catalyst and 2 molar equivalents of HCl (10 mL of 10 N HCl). After 1 hour, the pressure dropped by 8.5 psig of the expected 50 psig. Continued reduction overnight yielded a mixture which still contained 2.1% of the starting material. An additional 50 mg of catalyst was added and reduction continued for another several hours, at which point 0.79% of the starting material remained, as estimated from GC analysis.

The product mixture was filtered through Celite to remove the catalyst and the filtrate was stripped to an oil before water and 3.6 gm of $Na_2CO_3$ were added. The aqueous mixture was extracted with a total of 100 mL of hexane, which was dried and stripped under vacuum to yield 7.87 gm of product oil, 97.6%.

To 210 mL of concentrated sulfuric acid pre-cooled with an external water ice bath to 12 C in a 1 liter flask was added 31 gm of 2,3,3-trimethyl-dihydroindole, dropwise over 35 minutes so as to maintain a reaction temperature of between 12 and 17 C. The external bath was removed and powdered dry ice was then added directly to the mixture until the internal temperature was −8 C, at which point a room temperature mixture of 19.8 gm of sulfuric acid and 70% nitric acid was added dropwise over 20 minutes as the temperature continued to drop to −17 C. A temperature range of −17 to −22 C was maintained over the next hour by periodic addition of powdered dry ice. The reaction mixture was then poured onto 2.5 kg of ice, and 650 gm of 50% NaOH was added slowly with stirring to yield a yellow suspended solid, 6-nitro-2,3,3-trimethyl-dihydroindole, as shown below.

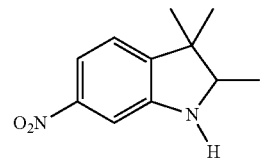

The solid was subsequently filtered and washed with 1 liter of water, and then set out to dry for about 3 days.

A mixture of 6-nitro-2,3,3-trimethyl-dihydroindole, 3.386 gm, 3-nitrobenzyl bromide, 3.9 gm, diisopropylethylamine, 2.33 gm, and 19 mL of DMF were heated in a 91° C. oil bath for 8 hours, at which point nearly all of the starting dihydroindole had been consumed as shown by both TLC and GC. The cooled mixture was added to 200 mL of water and stirred 2 hours. The aqueous layer containing the di-nitro product was decanted from the orange gum, and then back extracted with ethyl acetate. The gum was dissolved in about 45 mL of ethanol at reflux, and the mixture deposited orange crystals upon cooling to room temperature. The supernatant was decanted off and the crystals were air dried to give 4.54 gm (81%) as a first crop. The previous ethyl acetate back extracted solution and the EtOH supernatent were combined and stripped to dryness to give another 0.53 gm (9.5%) of di-nitro product. The two crops were combined and a portion of the combined crops was used directly for the next step.

A mixture of 1.0 gm of 6-nitro-N-(3-nitrobenzyl)-dihydroindole, 25 mL ethanol, and 64 mg of 10% palladium on carbon was hydrogenated in a Parr shaker at room temperature overnight to give complete conversion of the starting material to 95.2% of the di-amine and 4.8% unknowns by GC. After catalyst removal and stripping, 0.94 gm (114%) of the di-amino gum was obtained and used directly for the next step.

The 0.94 gm of 6-amino-N-(3-aminobenzyl)-dihydroindole isolated as a gum in the previous step was dissolved with 12 mL of methylene chloride and 0.89 gm of diisopropylethylamine, and cooled in a dry ice bath to −58 C. Benzoyl chloride, 0.86 gm, was added dropwise over 10 minutes, while maintaining −55° C. or colder. After about 45 minutes, 1 mL of methanol was added and to the reaction flask, the cold bath was removed, and after warming to room temperature over 2 hours, the solution was stripped to 3.16 gm of crude oil. The oil was treated with methylene chloride and water to give a slurry, which was filtered directly without separation of the liquid phases. The solid was washed with methanol and air dried to give 0.82 gm of the bis(benzamide) product, i.e., 6-benzamido-N-(3-benzamidobenzyl)-dihydroindole, as shown below.

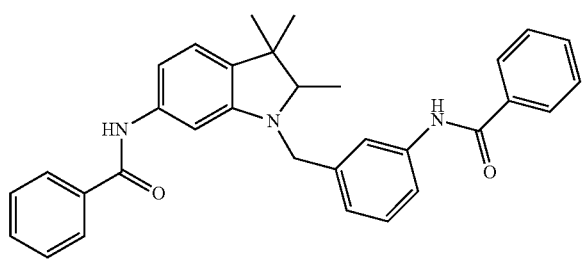 [SMILES: CC1N(Cc2cccc(NC(=O)c3ccccc3)c2)c2cc(NC(=O)c3ccccc3)ccc2C1(C)C]

A second crop of 0.30 gm was obtained from the filtrate by extraction with methylene chloride and concentration under vacuum.

A mixture of 2.06 gm of 6-benzamido-N-(3-benzamidobenzyl)-dihydroindole, 0.24 gm of squaric acid, 1.87 gm of triethylorthoformate and 30 mL of ethanol were heated to reflux in a 50 mL flask for 3.5 hours. After cooling to room temperature, the fine suspension was filtered and the solid, which is compound (IV) and shown below, was washed with ethanol. The dried solid, 1.62 gm, represents a 74% yield.

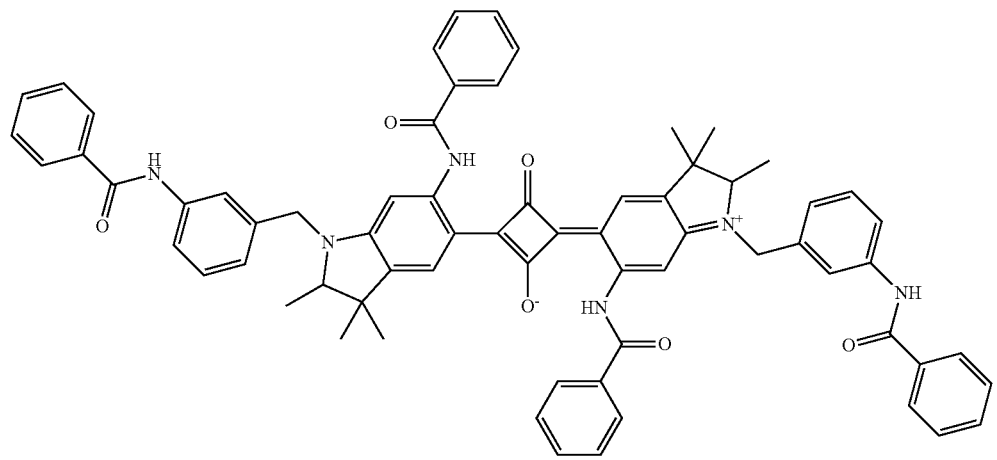 [SMILES: CC1N(Cc2cccc(NC(=O)c3ccccc3)c2)c2cc(NC(=O)c3ccccc3)c(C3=C([O-])/C(=c4/cc5c(cc4NC(=O)c4ccccc4)=[N+](Cc4cccc(NC(=O)c6ccccc6)c4)C(C)C5(C)C)C3=O)cc2C1(C)C]

By following similar reactions with the corresponding 2-nitrobenzyl bromide or 4-nitrobenzyl bromide, the corresponding 6-benzamido-N-(2 or 4-benzamidobenzyl)-dihydroindolines may be prepared. Furthermore, by following conditions similar to those used with squaric acid, these isomers may be used singly to form dyes of one regioisomer, or mixed to yield a mixture of related dyes, with 2-, 3-, and/or 4-benzamido substitution on each benzyl group.

Subsequent conversion to the squarylium dye can yield desirable photophysical, solubility, thermal stability, and/or light stability properties. For example, as shown in the FIG-URE, the ortho-, ortho- isomer of compound IV has a solubility of about 0.2 gm/L in dichloromethane, $CH_2Cl_2$. In comparison, the corresponding meta-, meta- and para-, para- isomers of compound have solubilities of about 0.6 gm/L and about 0.5 gm/L in $CH_2Cl_2$, respectively. And a mixture of isomers of compound IV prepared from a starting mixture of amine bases in a ratio of about 1:7:2 of ortho- : meta- : para- showed an unexpectedly high solubility of about 92 gm/L in $CH_2Cl_2$, over 100 times higher than the pure isomers.

EXAMPLE 2

5.75 gm of trifluoromethanesulfonic acid anhydride was added dropwise to a mixture of 3.22 gm of 6-amino-1,2,3,3-tetramethyl-dihydroindole in 25 mL of methylene chloride and 3.28 gm of diisopropylethylamine at −60 to −70° C. 6-amino-1,2,3,3-tetramethyl-dihydroindole was prepared as described in U.S. Pat. No. 5,543,086, which is expressly incorporated by reference herein in its entirety. This mixture was warmed to room temperature, poured into water, and extracted with ethyl acetate. The organic layer was dried with magnesium sulfate, filtered, and the solvent was stripped to an oil producing 6-Trifluoromethanesulfonamido-1,2,3,3-tetramethyl-dihydroindole, which is shown below and was used directly for dye synthesis.

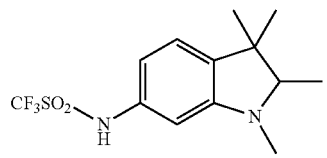

6-Trifluoromethanesulfonamido-1,2,3,3-tetramethyl-dihydroindole, 6.3 gm, was combined with 1.11 gm of squaric acid and 8.7 gm of triethylorthoformate in 70 mL ethanol at room temperature and the mixture was heated to reflux for 6 hours. The resulting crystals were collected and washed with ethanol. The peak absorption wavelength of the resulting squarylium dye, which is shown below, was 697 nm in methylene chloride, about 1 nm shorter in wavelength than the corresponding acetamide.

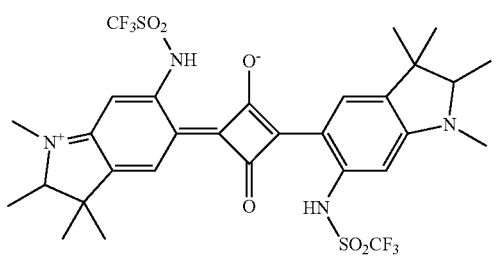

A related dye in which trifluoroacetamide replaced trifluoromethane-sulfonamide was prepared by a similar procedure from 6-amino-1,2,3,3-tetramethyl-dihydroindole. The peak absorption wavelength of this dye in methylene chloride was found to be 703.0 nm, about 7 nm longer in wavelength than the previous example. The longer peak absorption wavelength was unexpected, as electron withdrawing groups were expected to result in a shift to shorter wavelengths.

The squarylium dyes of the present invention may be used in inks, ink pens (e.g., Crayola™ markers), light filter materials or light filters, either alone or in combination with other dyes, stabilizers, additives, and polymers, either molecularly dispersed or as a component in an organic pigment. The squarylium dyes may be used, for example, with light sources that emit light at wavelengths greater than about 600 nm or with detectors that are sensitive to wavelengths greater than about 600 nm. The light filter materials or light filters may take the form of lenses, spectacles, or visors, for absorption of light otherwise incident to the eye, or as filters to reduce the intensity of wavelengths of light incident onto an electronic light detector.

The squarylium dyes of the present invention may be a fluorescent component in emissive materials or devices, applied singly or in combination with other dyes, stabilizers, additives, and polymers. In one example, the emissive device is a chemiluminescent device, e.g., a glow stick. The squarylium dyes may be used, for example, with light sources that emit light at wavelengths greater than about 600 nm or with detectors that are sensitive to wavelengths greater than about 600 nm.

The squarylium dyes of the present invention may impart nonlinear optical properties to materials and devices.

The emission properties of squarylium dyes as well as the excitation and detection of a fluorescent signal from squarylium dyes may be utilized in devices including, but not limited to, biological probes, tags (e.g., a security or identity tag), or fluorescent reporters.

The squarylium dyes of the present invention may act as singlet oxygen sensitizers for photodynamic therapy.

In other embodiments, the squarylium dyes may be used in photovoltaic devices that can convert incident light to electricity. For example, the dyes may be combined with electrodes and solvents and other components, such that upon application of light, a voltage is generated. In another example, the dyes may be used as a photoconducting component.

The squarylium dyes of the present invention may also be used for authentication or identification of an article including, but not limited to, a cash receipt, bank or personal check, and the like, or an article with a symbol, including symbols which identify the article as authentic, and including symbols encoding information, e.g., a bar code, 2D bar code, or QR code. In one example, the dyes may be directly imprinted onto the article or added to or mixed into the article during manufacture thereof. To authenticate and/or identify the article with the squarylium dye(s), the squarylium dye(s) may be illuminated, such as by semiconductor light sources, then the emissions detected, such as by cameras or photodiodes.

Squarylium dyes of the present invention, either symmetric or asymmetric, as single compounds or as a mixture of compositional and/or regioisomers, can provide for increased flexibility in dye design, especially for applications that require control of solubility and/or wavelength. Whereas certain single isomers, such as those of compound IV, show lower solubility, mixtures of isomers may show solubilities as much as about 100 times higher.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, any representative apparatus, device, or method, and illustrative examples shown and described. Accordingly, departures may be made from such details without departing from the spirit or scope of applicant's general inventive concept.

What is claimed is:

1. A squarylium dye having the formula (III)

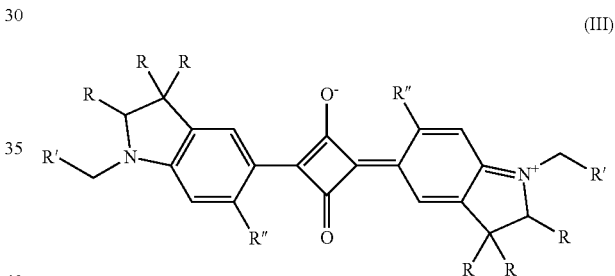

(III)

wherein
each R group is independently selected from the group consisting of hydrogen, alkyl, and alkylether, wherein at least three R groups are not hydrogen;
each R' group is independently selected from the group consisting of alkyl, aryl, alkylsulfonate, arylsulfonate, alkylcarboxylate, and arylcarboxylate;
each R" group is independently selected from the group consisting of amine, sulfonamide, carbamate, amide, urea, and hydroxyl, wherein when each R' group is alkyl, both R" groups cannot be an amide;
and mixtures thereof.

2. The dye of claim 1 wherein at least one R group is alkyl.

3. The dye of claim 1 wherein at least one R group is methyl.

4. The dye of claim 1 wherein at least one R' group is aryl.

5. The dye of claim 1 wherein each R' group is a substituted or unsubstituted phenyl.

6. The dye of claim 1 wherein at least one R" group is selected from:
(a) an amine defined by —$NR_aR_b$, where $R_a$ and $R_b$ are independently selected from hydrogen, substituted or unsubstituted alkyl, or substituted or unsubstituted aryl;
(b) an amide defined by —$NHCOR_e$, where $R_e$ is selected from a substituted or unsubstituted alkyl, a substituted or unsubstituted aryl, or a haloalkyl;

(c) a carbamate defined by —NHCO$_2$R$_f$, where R$_f$ is selected from a substituted or unsubstituted alkyl, a substituted or unsubstituted aryl, or a haloalkyl;

(d) a urea defined by —NHCONR$_g$R$_h$, where R$_g$ and R$_h$ are independently selected from hydrogen, a substituted or unsubstituted alkyl, a substituted or unsubstituted aryl, or a haloalkyl; or (e) a sulfonamide defined by —NHSO$_2$R$_i$, where R$_i$ is selected from a substituted or unsubstituted alkyl, a substituted or unsubstituted aryl, or a haloalkyl.

7. The dye of claim 1 wherein each R is methyl, each R' is benzamidophenyl, and each R" is benzamide.

8. A device including the dye of claim 1.

9. The device of claim 8 selected from a light filter, fluorescent probe, lens, spectacle, or visor.

10. An organic pigment including the dye of claim 1.

11. An ink or ink pen including the dye of claim 1.

12. A method for increasing the solubility of a squarylium dye comprising:
reacting three or more amine bases with squaric acid or a derivative thereof to yield a mixture of squarylium dyes, wherein the solubility of the squarylium dye mixture is 5 or more times greater than the solubility of the least soluble symmetric squarylium dye in the mixture.

13. The method of claim 12 wherein the squarylium dye mixture includes symmetric squarylium dyes that exhibit peak absorption wavelengths within about 50 nm of a desired wavelength.

14. The method of claim 12 wherein the amine bases are regioisomers.

15. A squarylium dye mixture formed by reacting three or more amine bases with squaric acid or a derivative thereof to yield a mixture of squarylium dyes, wherein the solubility of the squarylium dye mixture is 5 or more times greater than the solubility of the least soluble symmetric squarylium dye in the mixture.

16. A device including the dye of claim 15.

17. The device of claim 16 selected from a light filter, fluorescent probe, lens, spectacle, or visor.

18. An organic pigment including the dye of claim 15.

19. An ink or ink pen including the dye of claim 15.

20. A method for authentication or identification of an article comprising:
illuminating an article including a squarylium dye having the formula (III)

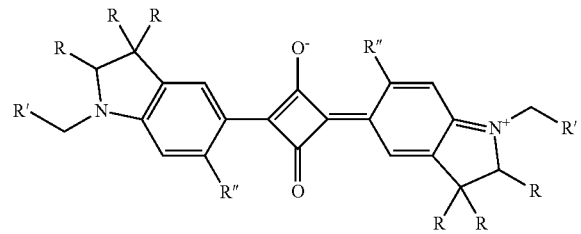

wherein
each R group is independently selected from the group consisting of hydrogen, alkyl, and alkylether, wherein at least three R groups are not hydrogen;
each R' group is independently selected from the group consisting of alkyl, aryl, alkylsulfonate, arylsulfonate, alkylcarboxylate, and arylcarboxylate;
each R" group is independently selected from the group consisting of amine, sulfonamide, carbamate, amide, urea, and hydroxyl, wherein when each R' group is alkyl, both R" groups cannot be an amide;
and mixtures thereof; and
detecting emission from the article.

21. A method for authentication or identification of an article comprising:
illuminating an article including a squarylium dye mixture formed by reacting three or more amine bases with squaric acid or a derivative thereof to yield a mixture of squarylium dyes, wherein the solubility of the squarylium dye mixture is 5 or more times greater than the solubility of the least soluble symmetric squarylium dye in the mixture; and
detecting emission from the article.

* * * * *

UNITED STATES PATENT AND TRADEMARK OFFICE
CERTIFICATE OF CORRECTION

| | | |
|---|---|---|
| PATENT NO. | : 9,090,776 B2 | |
| APPLICATION NO. | : 14/017359 | |
| DATED | : July 28, 2015 | |
| INVENTOR(S) | : Steppel et al. | |

It is certified that error appears in the above-identified patent and that said Letters Patent is hereby corrected as shown below:

In the Specification:

Column 7, line 8, "ROCOH" should read --ROCONH--

Signed and Sealed this
Ninth Day of February, 2016

Michelle K. Lee
*Director of the United States Patent and Trademark Office*